(12) United States Patent
Agustinos et al.

(10) Patent No.: US 12,114,937 B2
(45) Date of Patent: Oct. 15, 2024

(54) METHOD OF LOCATING A MOBILE PERCEPTION DEVICE INTENDED TO BE WORN OR CARRIED BY A USER IN A SURGICAL SCENE

(71) Applicant: PIXEE MEDICAL, Besançon (FR)

(72) Inventors: Anthony Agustinos, Devecey (FR); Luis Contreras, Besançon (FR); Alix Leroy, Besançon (FR)

(73) Assignee: PIXEE Medical, Besançon (FR)

( * ) Notice: Subject to any disclaimer, the term of this patent is extended or adjusted under 35 U.S.C. 154(b) by 0 days.

(21) Appl. No.: 17/880,255

(22) Filed: Aug. 3, 2022

(65) Prior Publication Data

US 2023/0049640 A1 Feb. 16, 2023

Related U.S. Application Data

(60) Provisional application No. 63/229,316, filed on Aug. 4, 2021.

(51) Int. Cl.
| | |
|---|---|
| *G06F 3/00* | (2006.01) |
| *A61B 34/10* | (2016.01) |
| *A61B 34/20* | (2016.01) |
| *A61B 90/00* | (2016.01) |

(52) U.S. Cl.
CPC .............. *A61B 34/20* (2016.02); *A61B 34/10* (2016.02); *A61B 2034/2055* (2016.02); *A61B 2090/365* (2016.02)

(58) Field of Classification Search
CPC ...... A61B 2034/107; A61B 2034/2051; A61B 2034/2055; A61B 2034/2059; A61B 2034/2063; A61B 2090/365; A61B 2090/373; A61B 2090/395; A61B 34/20; A61B 34/25; A61B 90/20; A61B 90/25; A61B 90/361; A61B 90/37; G06F 3/011; G06F 3/012; G06F 3/04815; G06T 19/006; G02B 21/0012
See application file for complete search history.

(56) References Cited

U.S. PATENT DOCUMENTS

| | | | |
|---|---|---|---|
| 2019/0183577 A1* | 6/2019 | Fahim | G02B 27/01 |
| 2021/0137623 A1* | 5/2021 | Yen | A61B 34/74 |

OTHER PUBLICATIONS

Yaniv, "Which Pivot Calibration?", in "Medical imaging 2015: Image-guided procedures, robotic interventions, and modeling", Eds. Yaniv et al., Proc of SPIE, 2015, vol. 9415, pp. 941527-1 to 941527-9 (note: in English; cited in the Specification).

* cited by examiner

*Primary Examiner* — Insa Sadio
(74) *Attorney, Agent, or Firm* — Seckel IP, PLLC

(57) ABSTRACT

The method of locating at least one mobile perception device of a navigation platform, the mobile perception device intended to be worn or carried by a user in a surgical scene, the navigation platform including at least one perception sensor, comprises: —acquiring, by the at least one perception sensor, a plurality of successive images of the scene including the portion of the body of the patient intended to be subjected to the surgical operation; —processing the plurality of successive images to evaluate a relative position of the mobile perception device and the portion of the body intended to be subjected to the surgical operation, wherein the relative position of the mobile perception device and the portion of the body takes into account a movement of the mobile perception device.

20 Claims, 4 Drawing Sheets

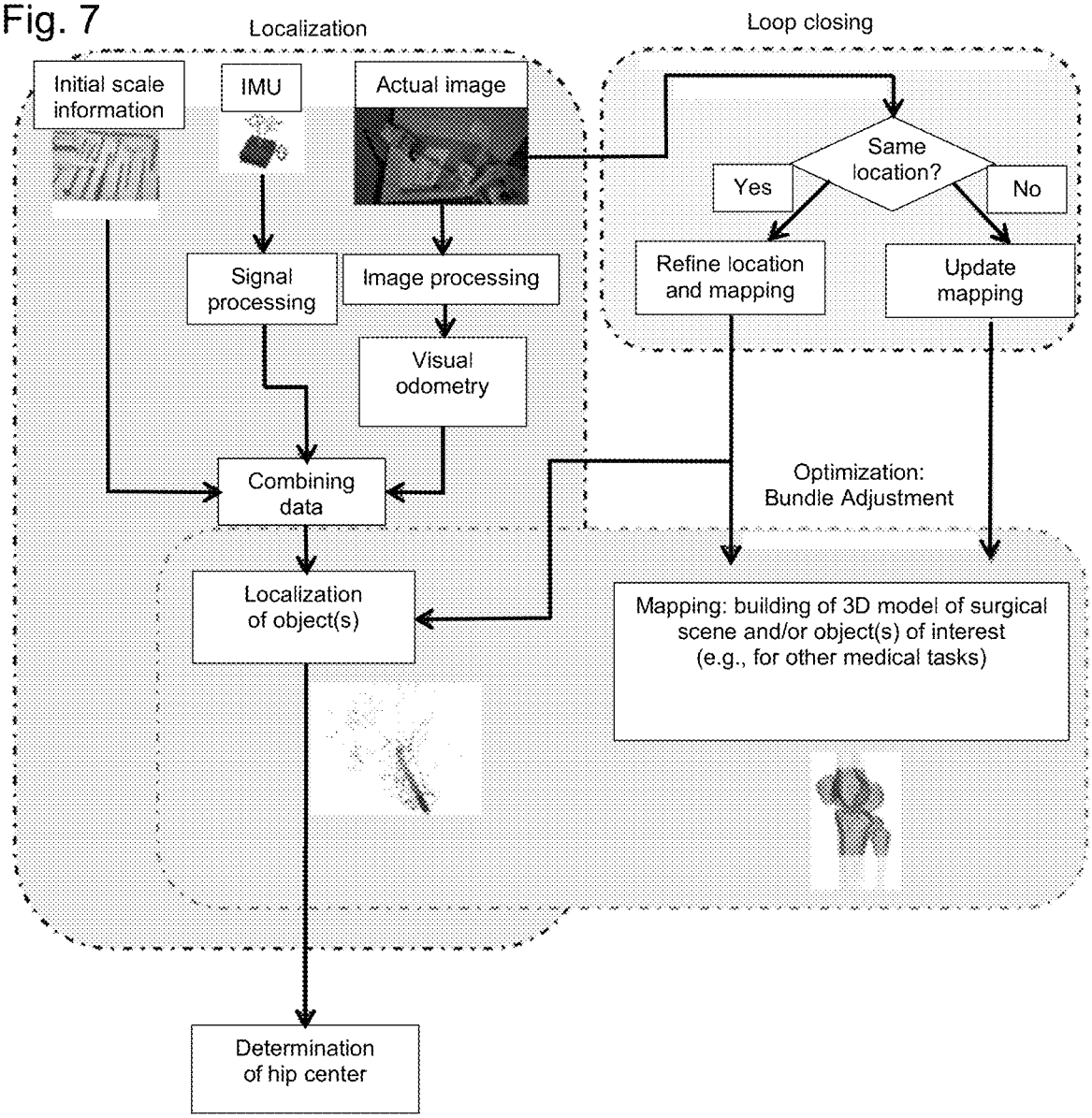

METHOD OF LOCATING A MOBILE PERCEPTION DEVICE INTENDED TO BE WORN OR CARRIED BY A USER IN A SURGICAL SCENE

RELATED APPLICATION

This application claims priority of provisional application No. 63/229,316 filed Aug. 4, 2021, whose content is hereby incorporated by reference herein in its entirety.

FIELD OF THE INVENTION

The invention relates to computer vision and augmented reality, applied to a surgical operation. Non-limitative examples of surgical operations include orthopedic surgery, such as the fitting of knee, hip, or shoulder prostheses.

BACKGROUND ART

Standard navigation systems for the three-dimensional tracking of objects are generally based on the use of infrared industrial cameras mounted in pairs in a stereoscopic configuration. Infrared emitters illuminate markers which are detected by the sensors. The 3D localization of objects is estimated by triangulation from the detection and matching of the markers.

Other similar systems are based on the use of a single active infrared camera and markers. The 3D localization of the objects is estimated via the geometric model of the camera, with knowledge of the 3D geometry of the markers and their position in the image.

SUMMARY OF THE INVENTION

In one aspect of the present invention, a method is provided that enables the acquisition of anatomical references by mobile perception devices such as connected glasses, tablets, smartphones, etc.

In another aspect, a method of locating at least one mobile perception device intended to be worn or carried by a user in a surgical scene makes it possible to eliminate the constraint of using an additional fixed reference marker within the framework of a mobile perception and/or navigation system.

In another aspect, a plurality of successive images are processed to evaluate a relative position of the mobile perception device and the portion of the body intended to be subjected to the surgical operation. A relative position of the mobile perception device and the portion of the body is then calculated so as to take into account a movement of the mobile perception device.

In another aspect, the mobile perception device includes an augmented reality display adapted to be worn or carried by a user, such as connected glasses, smartphone, tablet or any other type of mobile device, advantageously equipped with a display device, located in or close to an operating scene.

In another aspect, a program for controlling the system can be stored on a non-transitory computer-readable data storage medium, such as a memory of the system.

BRIEF DESCRIPTION OF THE DRAWINGS

Further aspects of the invention will be described in reference to the appended drawings which illustrate non-limiting exemplary embodiments, and among which:

FIG. 7 is a schematic view illustrating a second methodology "SLAM" for estimating the position of the pivot center of the hip, without using a fixed reference marker.

DETAILED DESCRIPTION OF PARTICULAR EMBODIMENTS

For non-limiting illustrations of the invention, exemplary embodiments of the invention will be described in the context of an application for the estimation of the hip center in knee prosthesis surgery. Applications of the invention are of course not limited to any particular type of surgical operation, on any portion of the body of any type of patient.

These methods can be applied to any perception device, integrating one or more sensors of various technologies, especially visual sensors, more particularly optical sensors, such as RGB camera, infrared camera, monochrome camera, stereovision system by passive or active camera, LiDAR, RADAR, ultrasound devices, etc. A single sensor can be used, or a plurality of sensors using the same or different technologies.

An appropriate processor or processors and/or memory or memories for exploiting the images from the sensor or sensors can be integrated in the perception device or in a separate device of the perception and/or navigation system.

For example, in the context of knee prosthesis fitting surgery for a human patient, an essential step for the femoral part consists in estimating the mechanical axis of the femur. This mechanical axis is defined by the center of the femoral head and the distal center of the femur.

Figure 1:
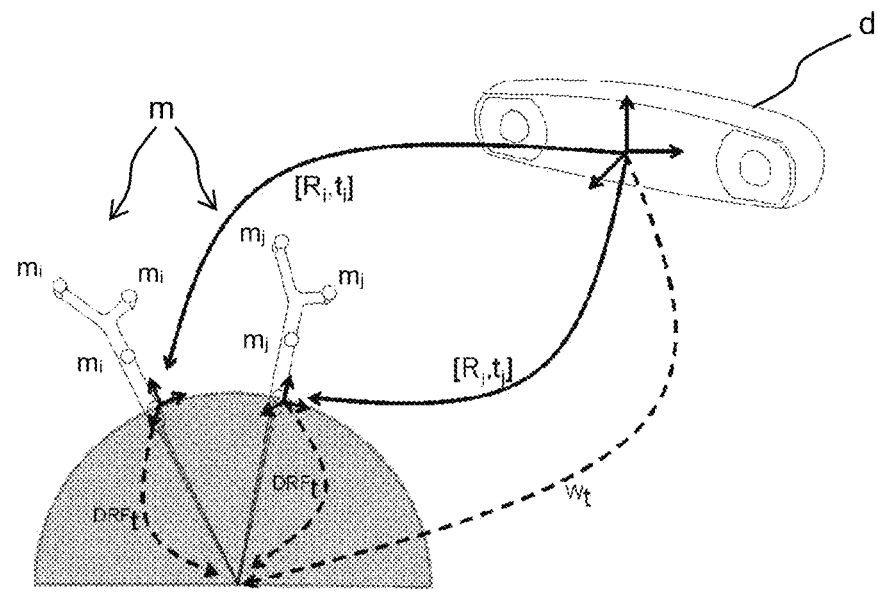
FIG. 1 is a schematic view of a knee operating scene illustrating a basic methodology for estimating the mechanical axis of the femur.

A basic methodology is illustrated on FIG. 1, which is based on Yaniv, Ziv, "Medical imaging 2015: Image-guided procedures, robotic interventions, and modeling", International Society for Optics and Photonics, 2015, p. 941527.

To estimate the three-dimensional position of the center of the femoral head:

Instruments including markers m are usually attached to the femur. Using these markers, the instruments can be localized in 3D in the reference frame of the perception device d (illustrated in FIG. 1).

This methodology considers three or more than three device acquisitions of these markers m for different positions (i, j . . . ) of the patient's leg, resulting in sets of 3D rigid geometric transformation [R, t] between marker and device coordinate system defined by a rotation matrix R (orientation) and a translation vector t (position) for different marker positions (i, j ...), as illustrated on FIG. 1.

From the set of 3D geometric transformations between marker and perception device referential frames, a pivot algorithm is typically used to solve the system. An iterative algorithm can be added to remove outliers.

As illustrated schematically on FIG. 1, the principle of a pivot algorithm is based on considering the femoral head as a perfect ball joint whose center can be assimilated to a fixed point. Thus, all the 3D geometric transformations between the markers and the reference frame of the vision device are estimated. From these transformations, the translation (DRFt) between the markers in each configuration and the pivot point can be estimated. Knowing this translation, the estimation of the translation of this pivot point (Wt) corresponding to the position of the center of the femoral head in the frame of reference of the vision device can then be determined.

Figure 2:
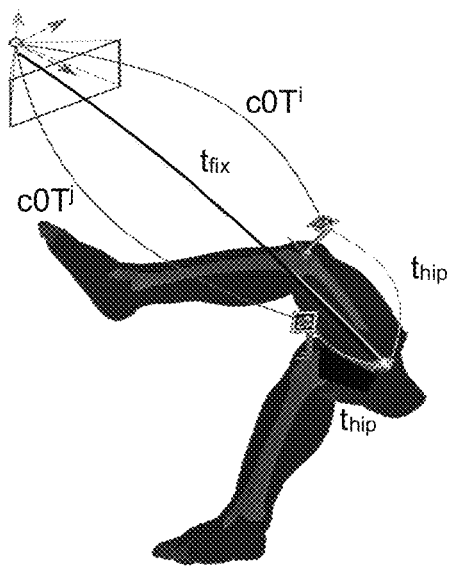
FIG. 2 is a schematic view illustrating a methodology for estimating the position of the pivot center of the hip with assumption of a fixed perception device.

FIG. 2 illustrates the method of estimating the position of the pivot center of the hip with assumption of a fixed perception device. A transformation between the perception device and the femoral head center is considered to be fixed $t_{fix}$. Transformations between markers and the hip center $t_{hip}$ are evaluated based on a plurality of 3D geometric transformations $c0T^i$ [$c0R_i$, $c0t_i$], $c0T^j$ [$c0R_j$, $c0t_j$], etc. between the markers and the reference frame of the vision device based on data acquisition (marker detection and 3D pose estimation) in varying positions (i, j, etc).

The feasibility of the basic methodology presented above relies on the assumption that the transformation between the frame of reference of the perception device and the hip center is rigid, i.e., a fixed patient and fixed sensor(s). In this case, all the measurements can be expressed in the same fixed frame of reference corresponding to that of the perception device. This constitutes a major constraint for the estimation of the hip center by these devices, to which is added a significant cost and bulk or even the need to respect the line of sight between the device and the markers.

Figure 3:
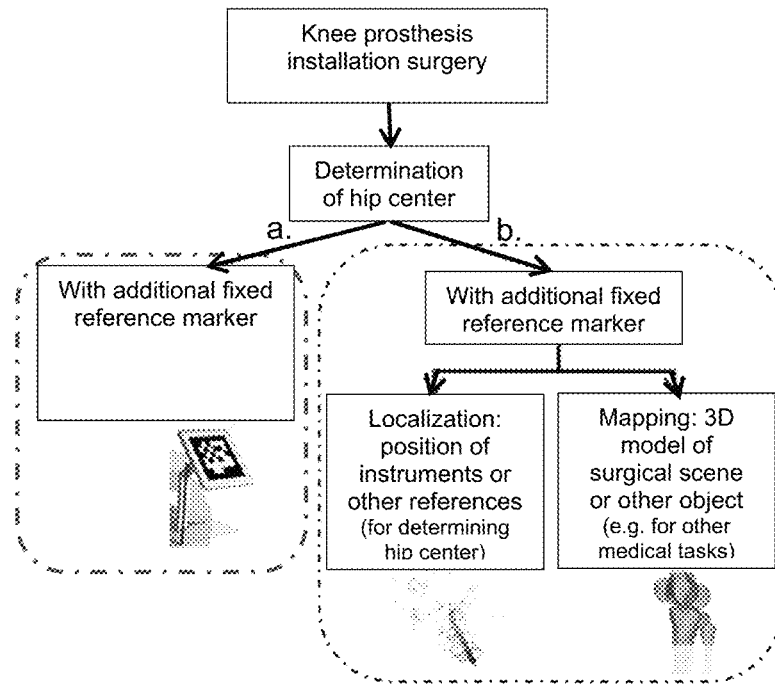
FIG. 3 is a flowchart representing an exemplary implementation of a method for estimating the hip center in knee prosthesis surgery, taking into account a mobility of the perception device.

FIG. 3 is a flowchart representing an exemplary implementation of methods according to the invention for improving the estimation of the hip center in knee prosthesis surgery, taking into account a mobility of the perception device. The examples of FIG. 3 correspond to an application of the method to the determination of the hip center for knee replacement surgery.

a. Use of an Additional Fixed Reference Marker

In a first embodiment, shown to the left of the flowchart of FIG. 3, a fixed additional frame of reference is set, in which all the measurements will always be expressed regardless of the movement of the device. This repository can be modeled, for example, by one or more marker(s) or even different objects in the environment of the operating scene that are easily identifiable by the sensor or sensors of the perception device. The pivot point calibration method is used to estimate the position and orientation of the hip center (pose) relative to a device's reference frame.

Figure 4:
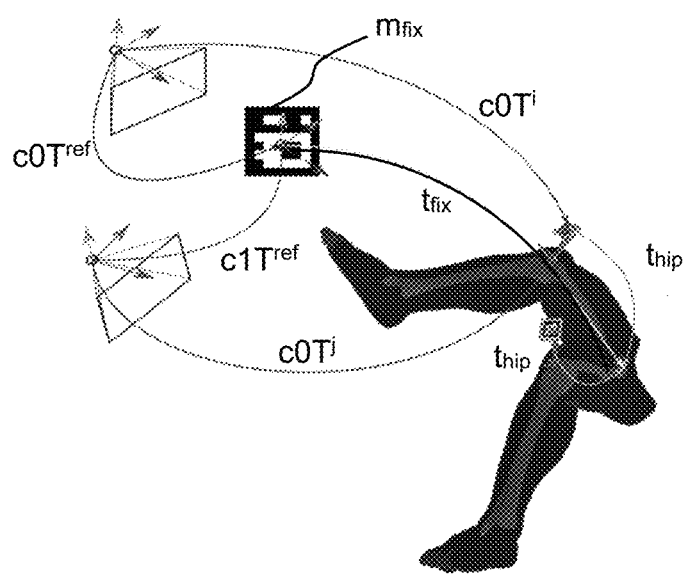
FIG. 4 is a schematic view illustrating a methodology for estimating the position of the pivot center of the hip, based on the use of an additional marker used as a fixed reference.

FIG. 4 illustrates more particularly a method of estimating the position in the context of a moving perception device, based on the use of an additional marker $m_{fix}$ used as a fixed reference, notably in relation to the patient's hip. Transformations between markers and the hip center $t_{hip}$ are estimated based on a plurality of data acquisitions from the mobile perception device $c1T^i$, $c0T^j$ corresponding to the 3D marker pose estimations (3D rigid transformations between marker and perception device reference frame for different positions of the perception device 0, 1, ... and the patient leg i, j, ...) in varying positions, and the transformation of the mobile perception device is evaluated relative to the fixed marker as $c1T^{ref}$, $c0T^{ref}$ in each of the varying positions.

b. Estimation of Device Motion without the Use of a Fixed Reference Marker

An alternative method of estimating the position of the pivot center of the hip does not rely on the use of fixed reference frames, making it possible to express all the measurements in the same reference frame to estimate the hip center while the device is in motion.

Figure 5:
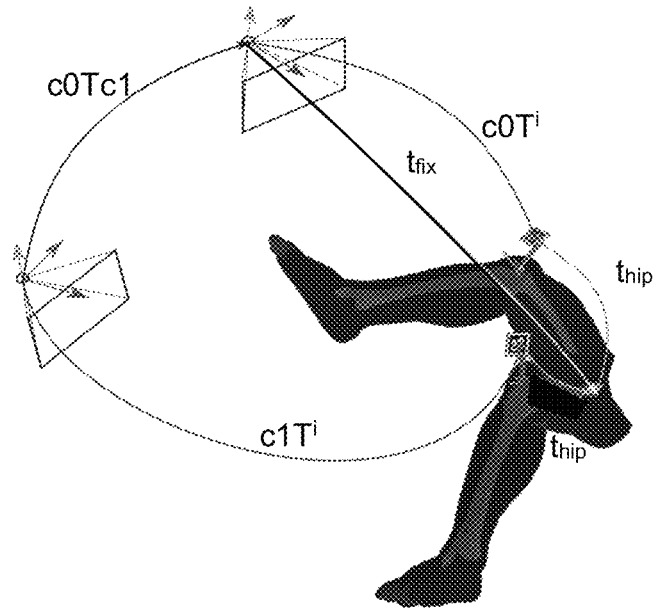
FIG. 5 is a flowchart representing an exemplary implementation of a method for estimating the hip center in knee prosthesis surgery, relying on estimating a relative position of the moving device relative to its initial position throughout the hip center position estimation procedure, without using a fixed reference marker.

FIG. 5 illustrates a method of this type, relying on estimating the relative position of the moving device relative to its initial position throughout the hip center position estimation procedure. Transformations between markers and the hip $t_{hip}$ are evaluated based on a plurality of data acquisitions from the mobile perception device $c1T^i$, $c0T^j$ in varying positions, and without using a fixed reference marker, the transformation of the mobile perception device is evaluated as c0Tc1 between the successive data acquisitions in the varying positions.

More particularly, for this purpose, advantageous embodiments of the invention rely on determining the relative movement (visual inertial odometry) of the device between different acquisitions. Other embodiments rely on locating the absolute position, such as simultaneous localization and mapping (SLAM) algorithm to determine the position of the device in its environment throughout the hip center position estimation procedure. Still other embodiments use both techniques, alternatively, successively, or simultaneously, as determined by an automatic or preset controller routine of the device, by the user, or both a controller of the device and the user.

b.1. Device Movement Estimation by Visual Odometry

The estimation of the relative position of the device involves determining its movement by odometry and can be obtained by different sensors: inertial measurement unit (IMU), one or more camera(s), RADAR, LiDAR, etc.

The data from the visual odometry and the external data is then fused, and the localization of the device and the instruments are calculated.

In a further step, the localization data of the device and instruments can be used as references data in the calculation of the hip pivot center.

In order to recover the pose (rotation and translation) of the perception device, an inertial measurement unit (IMU) rigidly linked to the device can be used. This IMU can include one or a plurality of sensors, typically three or more gyroscopes and three or more accelerometers by each coordinate axis. At each acquisition, the signals from these sensors make it possible to directly extract the three-dimensional movement of the device via the indirect estimation of the acceleration linear and angular velocity.

Figure 6:
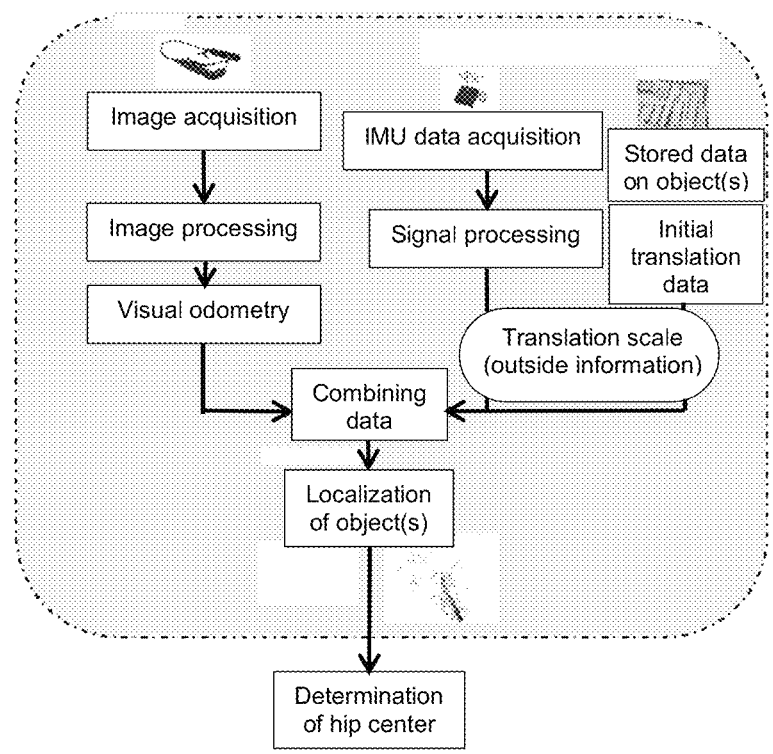
FIG. 6 is a schematic view illustrating a first methodology "visual odometry" for estimating the position of the pivot center of the hip, without using a fixed reference marker.

FIG. 6 illustrates the special case of visual inertial odometry applied to the calculation of the hip pivot center, using a camera and an IMU of augmented reality glasses.

In a first sequence, images are acquired and processed to recover up to an unknown scale factor the device pose estimate by using visual odometry.

In a second sequence, optionally, data is acquired from at least one inertial measurement unit (IMU) sensor, and the signal is processed. Previously stored data, for example, regarding previous movements of the device, can also be exploited, notably, to recover the scale factor. Alternatively, or additionally, preset data representative of a geometric model of a known object on the operation scene, such as a marker, an instrument, etc., can be exploited, to provide other external data on the initial scale factor.

b.2. Localization of the Device in its Environment

Various algorithms, such as simultaneous localization and mapping (SLAM) algorithms, make it possible to estimate the trajectory of a device in real time while reconstructing the observed environment in the form of a cloud of 3D points.

The mapping is the task for determining the map of the environment that may be totally unknown or partially unknown, using primitives that are easily identifiable in the sensor signals and a history of real positions of the device.

Alternatively, environment mapping can be built offline and used as a reference for localization. A progressive mapping procedure can also be used to improve an initial offline-built mapping.

Using the mapping, the localization of the device relies on estimating the position of the device in its environment using a history of acquisitions sequences and a knowledge of the environment mapping.

The localization of the device and/or the map can be refined by implementing an optimization process, such as bundle adjustment (BA). The BA is an optimization process to re-calculate the camera poses and map points using a group of image views.

A loop closing procedure can also be added to make it possible to recognize if the device has already passed through a position previously. All these procedures can be based on the use and combination of different sensors: one or more camera(s), IMU, RADAR, LiDAR, etc.

FIG. 7. illustrates an embodiment of a method relying on localization of the device in its environment implementing SLAM algorithm.

Three modules are present in this SLAM pipeline: Localization, Loop Closing and Bundle Adjustment.

In the first module named "Localization" the initial scale factor is obtained from the geometric model of a known object on the operation scene, such as a marker, an instrument, etc.

In a second sequence, optionally, data is acquired from the IMU, and the signal is processed to provide external data on the scale factor.

In a third sequence, images are acquired and processed to recover up to an unknown scale factor the device pose estimate by using visual odometry.

The data is combined and used to calculate the position of the device and/or other instruments.

In the second module named "Loop closing", a fourth sequence is present, the images acquired by the visual sensor are used to identify if the camera if the device has already passed through a position previously. This result will useful for the next module "Bundle Adjustment" to refine or increase the map.

In the last module "Bundle Adjustment", the localization of the device and instruments and/or the map will be refined.

As an optional result, the Bundle Adjustment module can provide a map as data representative of the operation scene. This map can be used to complement or to correct a 3D model of the operation scene.

In a final sequence, the hip pivot center is determined from the localization of the device and instruments.

In advantageous embodiments, the method of the invention utilizes low-cost monocular position estimation solutions, for example, connected glasses worn by the surgeon, smartphone, tablet or any other mobile device.

Embodiments of the invention can be designed to provide one or more of the following features:

for a user, typically a surgeon, reducing the clutter of the operating room with an excessive number of markers;

for a manufacturer or distributor, provide a technology that does not necessarily rely on one or more fixed markers, such as those used for the detection of the hip center during knee surgery, for example.

Accordingly, currently preferred embodiments of the invention utilize a monocular navigation system for the three-dimensional tracking of objects, without the need to use a fixed marker. For example, a mobile platform of the type augmented reality glasses, tablet, smartphone etc. is able to locate itself in the environment of the operating room by SLAM type approaches via the use of several sensors. This localization makes it possible to dispense with the use of a fixed reference to express all the measurements in the same frame of reference since the movement of the device can be determined between two acquisitions.

These approaches are advantageously based on the use of a sensor and/or a combination of different sensors of the same type or of different types: inertial measurement unit, one or more camera(s), RADAR, LiDAR, etc.

Advantageously, some embodiments can be designed to provide an optimized balance between obtaining sufficient precision in the estimation of the position of the perception device and having a fairly light software system running on a low-cost platform, such as with connected glasses worn by the surgeon, smartphone, tablet or any other mobile device.

The device is advantageously worn or carried by the surgeon. For example, augmented reality glasses by Vuzix, Rochester, N.Y., such as their model M400, can be used.

The augmented reality display can be a single 2D image view with superposed information, or an actual view by the eye of the user, with superposed information provided by the device, or even a virtual simulation of an actual view with superposed information, or any combination of these augmented reality displays. The virtual simulation of an actual view can be created based on an actual view, on a model, such as a 2D or 3D model, of the actual view, from a predefined model, such as a 2D or 3D model, or any combination of these simulations. A portion of an actual view or of an image of an actual view may be excluded or occluded in favor of the augmented reality information, such as by framing and/or covering.

The above disclosures, embodiments and examples are nonlimitative and for illustrative purposes only. In particular, the above description of the method in the context of the determination of hip center in preparation for knee surgery is for illustrative purposes. The invention finds application in other surgical circumstances as well as in other fields.

The invention claimed is:

1. A method of locating at least one mobile perception device of a navigation platform, the mobile perception device being adapted to be worn or carried by a user in a surgical scene in preparation to a surgical operation on a portion of a body of a patient forming part of the surgical scene, the mobile perception device including at least one perception sensor, the method comprising:

acquiring, by the at least one perception sensor, a plurality of successive images of the scene including the portion of the body of the patient intended to be subjected to the surgical operation;

processing the plurality of successive images to evaluate an evolution in time of a relative position of the mobile perception device and the portion of the body intended to be subjected to the surgical operation, wherein the evaluation of the evolution in time of the relative position of the mobile perception device and the portion of the body takes into account a movement of the mobile perception device.

2. The method according to claim 1, further comprising determining at least one anatomical reference of the patient from the plurality of successive images of the scene.

3. The method according to claim 1, wherein the movement of the mobile perception device is determined by visual odometry.

4. The method according to claim 1, wherein the movement of the mobile perception device is determined using visual simultaneous localization and mapping (SLAM) algorithm.

5. The method according to claim 1, wherein the user is a surgeon.

6. The method according to claim 1, wherein the patient is a human patient.

7. The method according to claim 6, wherein the surgical scene is a knee operation and the portion of the body of the patient includes at least part of a knee of the patient.

8. The method according to claim 7, wherein the successive images of the scene include the portion of the body of the patient in different positions of the knee.

9. The method according to claim 8, further comprising determining a hip center of the patient for the knee operation.

10. The method according to claim 1, wherein the at least one perception sensor is or are each independently selected from the group consisting of RGB cameras, infrared cameras, monochrome cameras, passive camera stereovision systems, active camera stereovision systems, LiDAR devices, RADAR devices, and ultrasound devices.

11. The method according to claim 1, wherein the at least one perception sensor includes or include one or more cameras.

12. The method according to claim 1, wherein the at least one perception sensor includes one or more cameras and one or more inertial movement units.

13. The method according to claim 1, wherein the at least one perception sensor includes a single camera.

14. The method according to claim 1, wherein the at least one perception sensor includes a single and one or more inertial movement units.

15. The method according to claim 14, wherein the mobile perception device includes a display device.

16. The method according to claim 15, herein the mobile perception device is selected from the group consisting of augmented reality glasses, tablets, and smartphones.

17. The method according to claim 1, herein the mobile perception device includes a display device.

18. The method according to claim 1, herein the mobile perception device is selected from the group consisting of connected glasses, tablets, and smartphones.

19. A navigation platform, comprising:
at least one mobile perception device, the mobile perception device being adapted to be worn by a user in a surgical scene in preparation to a surgical operation on a portion of a body of a patient forming part of the surgical scene,
the at least one mobile perception device including at least one perception sensor,
wherein the navigation platform is adapted to implement:
acquiring, by the at least one perception sensor, a plurality of successive images of the scene including the portion of the body of the patient intended to be subjected to the surgical operation;
processing the plurality of successive images to evaluate an evolution in time of a relative position of the mobile perception device and the portion of the body intended to be subjected to the surgical operation, wherein the evaluation of the evolution in time of the relative position of the mobile perception device and the portion of the body takes into account a movement of the mobile perception device.

20. A non-transitory computer-readable data storage medium on which is stored program comprising navigation instructions for a navigation platform, comprising:
at least one mobile perception device, the mobile perception device being adapted to be worn by a user in a surgical scene in preparation to a surgical operation on a portion of a body of a patient forming part of the surgical scene,
the at least one mobile perception device including at least one perception sensor,
wherein the program is adapted, when the program is run on a computer, to implement:
acquiring, by the at least one perception sensor, a plurality of successive images of the scene including the portion of the body of the patient intended to be subjected to the surgical operation;
processing the plurality of successive images to evaluate an evolution in time of a relative position of the mobile perception device and the portion of the body intended to be subjected to the surgical operation, wherein the evaluation of the evolution in time of the relative position of the mobile perception device and the portion of the body takes into account a movement of the mobile perception device.

* * * * *